US010292861B2

United States Patent
Gerg (10) Patent No.: US 10,292,861 B2
(45) Date of Patent: May 21, 2019

(54) ROTATIONAL ALIGNMENT OF FLUID DELIVERY DEVICE

(75) Inventor: James Gerg, Lake Forest, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 873 days.

(21) Appl. No.: 12/613,608

(22) Filed: Nov. 6, 2009

(65) Prior Publication Data

US 2011/0092888 A1    Apr. 21, 2011

Related U.S. Application Data (60) Provisional application No. 61/112,612, filed on Nov. 7, 2008.

(51) Int. Cl.
| | | |
|---|---|---|
| *A61F 9/007* | (2006.01) | |
| *A61M 1/00* | (2006.01) | |
| A61B 90/00 | (2016.01) | |
| A61B 17/32 | (2006.01) | |

(52) U.S. Cl.
CPC ...... *A61F 9/00736* (2013.01); *A61F 9/00745* (2013.01); *A61M 1/0084* (2013.01); *A61B 2017/320084* (2013.01); *A61B 2090/0807* (2016.02); *A61B 2090/0811* (2016.02); *A61M 2205/583* (2013.01); *A61M 2205/6018* (2013.01); *A61M 2205/6036* (2013.01); *A61M 2205/6045* (2013.01); *A61M 2205/6063* (2013.01); *A61M 2205/6081* (2013.01); *A61M 2210/0612* (2013.01)

(58) Field of Classification Search
CPC . A61B 2019/4857; A61B 2017/320084; A61F 9/00736; A61F 9/00745; A61M 1/0084; A61M 2205/583; A61M 2205/6081; A61M 2210/0612

USPC ................... 604/22, 264; 606/106
See application file for complete search history.

(56) References Cited

U.S. PATENT DOCUMENTS

| | | | | |
|---|---|---|---|---|
| 3,093,134 | A * | 6/1963 | Roehr | 604/272 |
| 4,869,715 | A * | 9/1989 | Sherburne | 604/22 |
| 4,904,238 | A * | 2/1990 | Williams | A61M 1/0084 604/264 |
| 5,162,044 | A * | 11/1992 | Gahn et al. | 604/22 |
| 5,188,589 | A * | 2/1993 | Wypych | A61F 9/00745 604/22 |
| 5,242,385 | A * | 9/1993 | Strukel | 604/22 |
| 5,336,191 | A * | 8/1994 | Davis et al. | 604/165.01 |

(Continued)

FOREIGN PATENT DOCUMENTS

| | | |
|---|---|---|
| EP | 0583144 A1 | 2/1994 |
| EP | 1757236 A2 | 2/2007 |
| WO | 2009029131 A1 | 3/2009 |

*Primary Examiner* — Nathan R Price
*Assistant Examiner* — Anh Bui
(74) *Attorney, Agent, or Firm* — Johnson & Johnson Surgical Vision, Inc.

(57) ABSTRACT

A device configured for use in an ocular surgical procedure is provided. The device, such as a sleeve or a needle, includes a proximal portion, a distal portion including at least one fluid opening formed at a predetermined orientation, and at least one visual marking provided at the proximal portion at a predetermined marking orientation relative to said predetermined orientation. The visual marking or markings provide a visual indication of orientation of the fluid opening when the device is employed in the ocular surgical procedure.

20 Claims, 8 Drawing Sheets

(56) References Cited

U.S. PATENT DOCUMENTS

| | | | |
|---|---|---|---|
| 5,484,398 A * | 1/1996 | Stoddard | 604/22 |
| 5,643,276 A * | 7/1997 | Zaleski | 606/107 |
| 5,759,178 A * | 6/1998 | Wells | 604/240 |
| 5,957,928 A | 9/1999 | Kirwan, Jr. | |
| 6,117,126 A * | 9/2000 | Appelbaum et al. | 606/1 |
| 6,221,056 B1 * | 4/2001 | Silverman | 604/239 |
| 6,280,449 B1 * | 8/2001 | Blake | 606/107 |
| 6,299,591 B1 * | 10/2001 | Banko | 604/22 |
| 7,204,820 B2 * | 4/2007 | Akahoshi | 604/22 |
| 7,601,136 B2 * | 10/2009 | Akahoshi | 604/22 |
| 2003/0069594 A1 * | 4/2003 | Rockley et al. | 606/169 |
| 2003/0078591 A1 * | 4/2003 | Barrett | 606/107 |
| 2005/0234473 A1 * | 10/2005 | Zacharias | 606/107 |
| 2006/0100653 A1 | 5/2006 | Akahoshi | |
| 2006/0135975 A1 | 6/2006 | Perkins | |
| 2008/0009823 A1 * | 1/2008 | McKay | 604/500 |
| 2008/0281341 A1 * | 11/2008 | Miller et al. | 606/166 |
| 2008/0300531 A1 * | 12/2008 | Gills, Jr. | A61F 9/00736 604/22 |

* cited by examiner

ROTATIONAL ALIGNMENT OF FLUID DELIVERY DEVICE

BACKGROUND OF THE INVENTION

Field of the Invention

The present invention generally relates to fluid delivery devices employed for use with phacoemulsification needles and more specifically to orientation of such fluid delivery devices during surgical procedures.

Description of the Related Art

Phacoemulsification refers to a method of lens and cataract extraction from an eye. The procedure includes an ultrasonically vibrated needle which is inserted through a very small incision of the cornea in order to provide energy for fragmenting the lens and cataract which then can be aspirated and removed through the incision.

The needle is supported by a handpiece interconnected with a console which provides electrical power to the handpiece as well as a supply of irrigation fluid and a vacuum source for aspiration of fragmented tissue and liquids.

Certain current handpieces can provide fluid to the eye during the surgical procedure. In order to facilitate the flow of fluid to the eye, the handpiece and needle are typically provided with a sleeve, which can facilitate delivery of fluid to the eye through a path between the needle and the sleeve. Sleeves are typically formed of resilient yet pliable materials and include openings from which fluid emanates, typically two openings oriented 180 degrees apart. Silicone is typically employed in the construction of sleeves.

One issue with handpieces employing needles and sleeves is the proper orientation of the devices. When a surgeon uses a handpiece fitted with a sleeve, he frequently employs the sleeve and needle in a region of the eye wherein he cannot see the orientation of the sleeve and/or the two fluid openings or ports provided and thus does not know in which direction fluid flows during the surgical procedure. A surgeon typically views the procedure through a device such as a microscope, and her inability to see the orientation of the ports during the surgery can potentially raise at least two issues.

First, fluid flow toward certain parts of the eye chamber, such as the retina or cornea, can potentially harm those regions, while fluid flow toward other parts of the eye chamber can be essentially benign and permissible to properly perform the surgery.

Second, some surgeons wish to employ the fluid in conjunction with the needle to more rapidly acquire, break apart, and/or emulsify the cataract material. Such surgeons employ fluid flow and ultrasonic power in tandem, and if the surgeon does not know the orientation of fluid flow he runs the risk of moving the fluid in an undesired direction, for example pushing away material he wishes to work on and break up. Such an occurrence could potentially extend the duration of the surgery, and is undesirable.

Other fluid delivery devices are provided in ocular surgical environments. For example, vitrectomy devices, such as cutters, may provide fluid flow without use of a sleeve through ports in the device. Vitrectomy devices may also use a sleeve comprising one or more ports for providing fluid flow. Again, these ports may become obscured and the vitrectomy surgeon may be unable to establish the orientation of the ports when obscured or partially obscured.

Further, the typical phaco handpiece and needle may be operated without a sleeve but with a separate fluid handpiece. In this instance, the needle can aspirate fluid from the eye through an opening, but again obscuration of the tip can be an issue.

It would therefore be desirable to provide a phacoemulsification fluid delivery arrangement, such as a needle or needle arrangement including a sleeve, that tends to minimize the adverse aspects previously known in such devices.

SUMMARY OF THE INVENTION

According to one aspect of the present design, there is provided a device, such as a sleeve or a needle, configured for use in an ocular surgical procedure. The device comprises a proximal portion, a distal portion comprising at least one fluid opening formed at a predetermined orientation, and at least one visual marking provided at the proximal portion at a predetermined marking orientation relative to the predetermined orientation. The at least one visual marking provides a visual indication of orientation of the fluid opening when the device is employed in the ocular surgical procedure.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings in which.

DETAILED DESCRIPTION OF THE DESIGN

The following description and the drawings illustrate specific embodiments sufficient to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design is directed to a device configured for use in an ocular surgical procedure. The device, which may be a sleeve, a phacoemulsification ("phaco") needle, a vitrectomy cutter, or similar device, comprises a proximal portion, a distal portion comprising at least one fluid opening formed at a predetermined orientation, and at least one visual marking provided at the proximal portion at a predetermined marking orientation relative to the predetermined orientation. The visual marking(s) provide a visual indication to the surgeon of the orientation of the fluid opening when the device is employed in the ocular surgical procedure.

Figure 1:
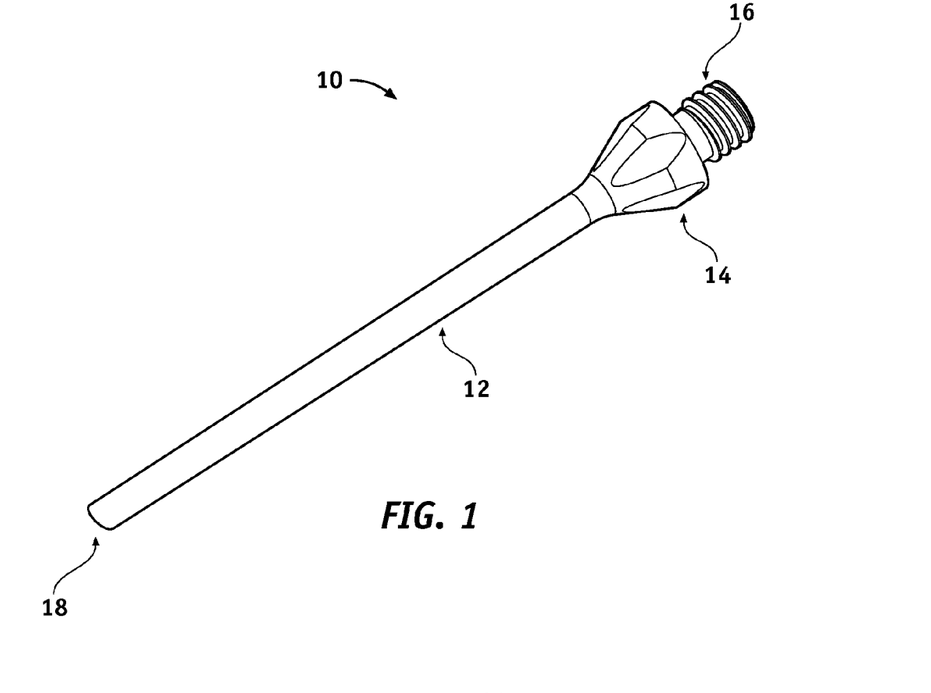
FIG. 1 is perspective view of a phacoemulsification needle in accordance with the present invention generally showing a needle body having a proximal portion and distal portion with a tip portion disposed at the end.

With reference to FIG. 1, there is shown a sample phacoemulsification needle 10 generally having a needle body 12 with a lumen (not shown) passing therethrough. Needle body 12 includes a proximal portion 14 which may include a threaded portion 16 which adapts the needle for attachment to a phacoemulsification handpiece, not shown.

Figure 2:
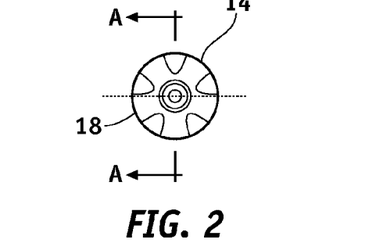
FIG. 2 illustrates an end view of the needle shown in FIG. 1.
Figure 3:
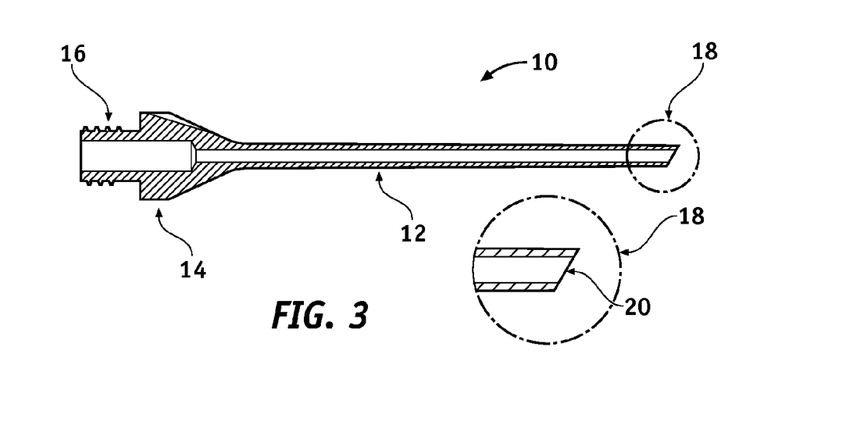
FIG. 3 is a cutaway representation of the needle highlighting the beveled tip of the needle.

A distal tip portion 18 of needle body 12 includes a beveled tip 20. FIG. 2 illustrates a view from the distal end of the needle 10, where proximal portion 14 and distal tip portion 18 are visible. FIG. 3 is a cutaway side view of needle 10 along line A-A of FIG. 2. FIG. 3 illustrates distal tip portion 18 with an expanded view showing beveled tip 20. Fluid is drawn from the eye through the beveled tip 20. As discussed, certain ocular surgical procedures can benefit from properly orienting the beveled tip 20 during a procedure.

As may be appreciated, the needle of FIGS. 1-3 is shown as a representative needle and other needle designs may be employed successfully with the current design. Any tip known in the art is envisioned to be employed in accordance with the present invention, such that orientation of the tip is provided. A needle as is shown in FIGS. 1-3 may be fitted with a sleeve as described herein, but other needles which employ sleeves may also be employed and are considered within the present teachings. Needle 10 of FIGS. 1-3 is therefore merely representative of the general class needles which may be employed with the present invention.

Figure 4A:
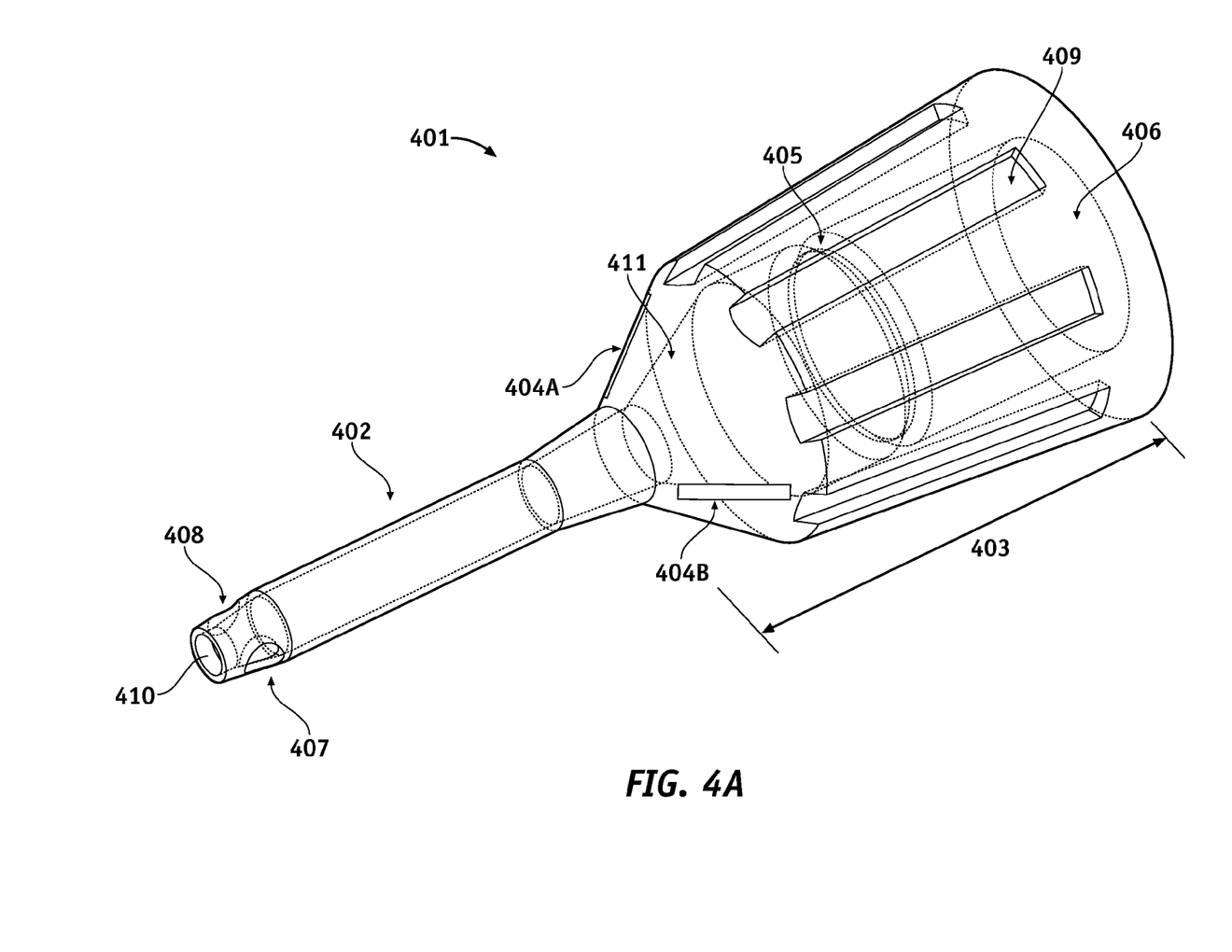
FIG. 4A illustrates a sleeve having a distal portion and a proximal portion together with at least one marking provided thereon.

FIG. 4A illustrates a sleeve 401 having a distal portion 402 and a proximal portion 403 together with at least one marking provided thereon, where FIG. 4A illustrates two markings 404A and 404B. Other parts of the sleeve are shown, such as internal ring 405 useful in holding sleeve 401 to a needle (not shown), centerline 406 representing the center of the sleeve 401, and port openings or openings 407 and 408. Fluid flows out of sleeve 401 from through port openings 407 and 408 when sleeve 401 is employed for its intended purpose with a needle. Notches such as notch 409 are provided to facilitate grip. The tip of a needle employed with sleeve 401 extends through opening 410. The sleeve shown in FIG. 4 may be employed with a phaco needle or a similar sleeve may be provided with a vitrectomy needle as desired. The same applies for all sleeves disclosed herein.

Marking 404B in FIG. 4A is shown as a simple line radiating in the direction of the axis of the needle, and may be of a particular color. Different types of markings, including different shapes, orientations, numbers of markings, and so forth may be provided as discussed below. Regarding color, marking 404A and/or 404B may be of a contrasting color to the locally surrounding product surface color, such as a black color marking 404A for a white color sleeve 401, or a dark red color marking 404A for a light green color sleeve 401, or a white color marking 404A for a dark blue color sleeve 401. Other marking color arrangements may be employed. Colored sleeves have been used to indicate different sleeve sizing, but again, markings or indicators 404A and/or 404B may be of contrasting or different color no matter the sleeve color.

As shown in FIG. 4A, certain stamping 411 of information has in the past been employed on the sleeve, typically to indicate a lot number or other inventory designation. The orientation of such stamping 411 has been arbitrary and does not provide any indication to the surgeon of the orientation of the port openings on the sleeve. A surgeon or assistant employing sleeve 401 with stamping 411 thereon has no idea where the ports are located based on the appearance or orientation of the stamping. Reliance on this arbitrary stamping to orient the ports is not generally feasible due to the uncertainty and imprecision of the stamping.

Regarding orientation of the markings such as markings 404A and 404B, any orientation of markings that assists the surgeon in providing desired fluid delivery or handpiece orientation is contemplated. One embodiment of the markings 404A and 404B is as shown in FIG. 4A, embodied as two stripes provided at 180 degrees apart from each other, with each marking radially oriented in line with a port opening, such as port opening 407 or 408. In this manner, as shown in FIG. 4B, sleeve 451 inside capsular bag 453 (typically circular in shape when viewed in a microscope) having its distal portion 452 beneath lens material such that port openings 457 and 458 are obscured but oriented horizontally or outward in the orientation shown result in marking 454 being oriented horizontally away from the surgeon when viewed in the typical environment (field of view 455), such as through a microscope.

Figure 4B:
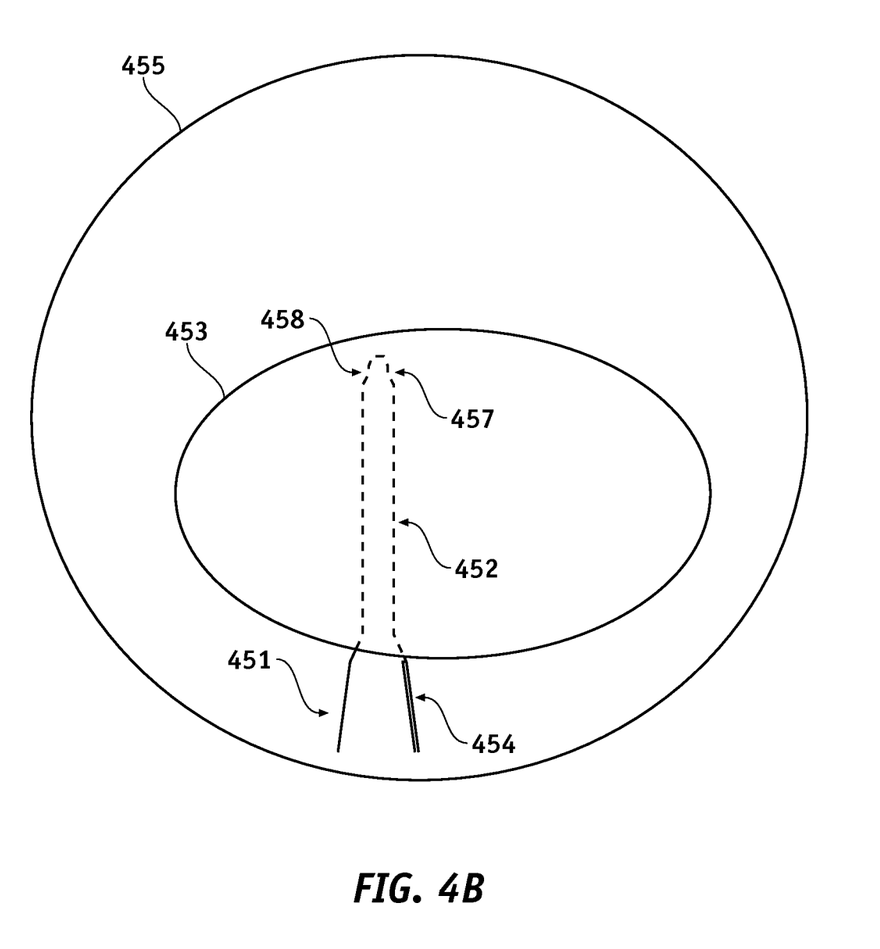
FIG. 4B illustrates the sleeve of FIG. 4A in an ocular surgical procedure as the sleeve might be viewed by a surgeon with a marking provided on the proximal portion of the sleeve.

In FIG. 4B, the markings are generally not visible, but marking 454 is provided at a far edge of the field of view, and the absence of a visual marking indicates that ports 457 and 458 are properly oriented. This orientation of markings, where the surgeon attempts to ensure that no marking is visible through the microscope, provides a visual cue to the surgeon to verify that the ports are oriented in the desired direction if, as here, orientation of the ports in a horizontal direction is desired.

Other markings and orientations may be provided, such as at different angles relative to the port openings, i.e. in line with the port openings so the desire is for the surgeon to not see markings when the distal tip is covered, or other orientations. The markings may take different forms, including but not limited to sets of lines, sets of dots, diagonal lines, circles, letters, numbers, or virtually any non-arbitrary visual indicator representing an orientation or a particular point on the sleeve. The markings may be provided in other forms, including but not limited to laser marking of the sleeve, grooves or indentations provided in the device, pad/silk screen printing, surface texturizing, embossed and debossed features such as molded or machined ribs and grooves, and so forth.

Alternative shapes that the user's eye can interpret as projecting a longitudinal path along the axis of a surgical device extension to a point distal to the marker representation including but not limited to a single dot, a plurality of axially oriented dots, stripes (longitudinally tapered and/or constant width and/or angled), arrows, triangles, and other geometric shapes of or plurality of shapes that interpreted together form a directional axis may be employed.

Further, while it is believed that markings 404A, 404B, and 454 may be on the proximal portion of sleeves 401 and 451, they may be positioned at multiple positions on the sleeve, such as the entire length of sleeve 401 or a significant portion of sleeve 401, or at the distal part of sleeve 401, or at a medial part of sleeve 401, or at any combination thereof. This is also true for markings on a phaco needle and vitrectomy devices, such as a cutter. Thus the markings are intended to be broadly interpreted to mean any visual cue viewable by a surgeon that may assist in the positioning of the device such as a needle and sleeve when employed in an ocular surgical procedure.

Use of the present markings can also provide for a desired orientation of the sleeve on the needle. Operating room personnel can sometimes misalign a sleeve on a needle such that the port openings on the sleeves are not properly oriented. The markings provided, such as markings 404A and 404B, can enable operating room personnel to quickly and accurately locate or position the sleeve on the needle.

Figure 5:
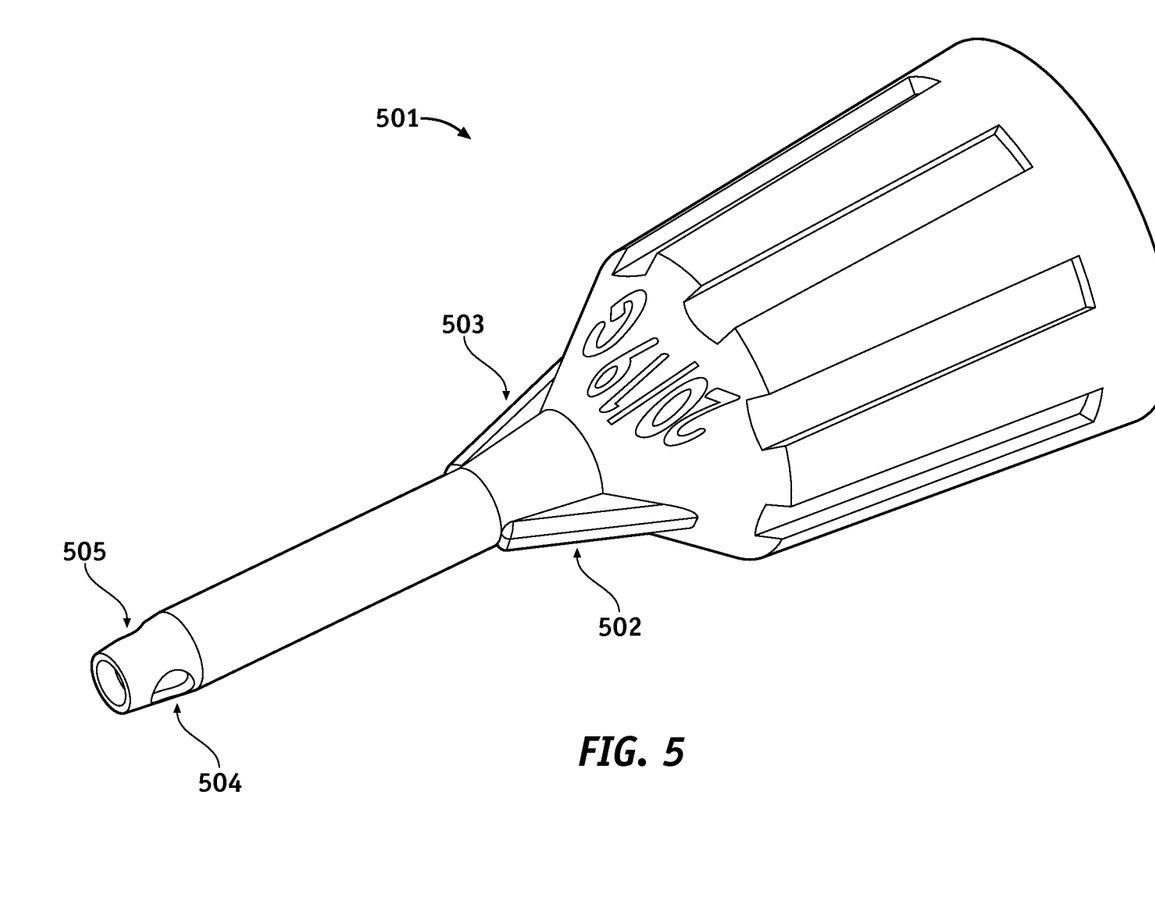
FIG. 5 shows the use of a sleeve such as is shown in FIG. 4 in an ocular surgical procedure where the distal portion is obscured by ocular material but the visual marking indicates a preferable orientation of the needle.

An alternate sleeve 501 is illustrated in FIG. 5. From FIG. 5, there is provided a pair of raised outer "ribs" 502 and 503 on sleeve 501. Raised outer ribs 502 and 503 are placed in an orientation such that an imaginary extended line along the long axis of ribs 502 and 503 directly pass through port locations 504 and 505.

Ribs or protrusions or other three dimensional markings may be beneficial in certain circumstances in that they may be readily seen under microscopes and may provide a clearer indication of the sleeve, port, and needle positions in certain environments. Again, ribs may be provided in different form, in different orientations, and/or in different positions from those shown, but generally represent visual indicators that can be relied on by a surgeon or operator to align the sleeve, phaco needle, handpiece, and/or vitrectomy cutter. The orientation in FIG. 5 is that ports 504 and 505 are aligned with ribs 502 and 503, but ribs 502 and 503 may be oriented in a different arrangement, such as that shown in FIG. 6, namely 180 degrees apart but 90 degrees from the port openings at the distal portion of the sleeve, similar to the markings in FIG. 4. Further, the ribs of FIG. 5 may be of the same color as the sleeve or may be of a different color, and may take different forms.

Figure 6:
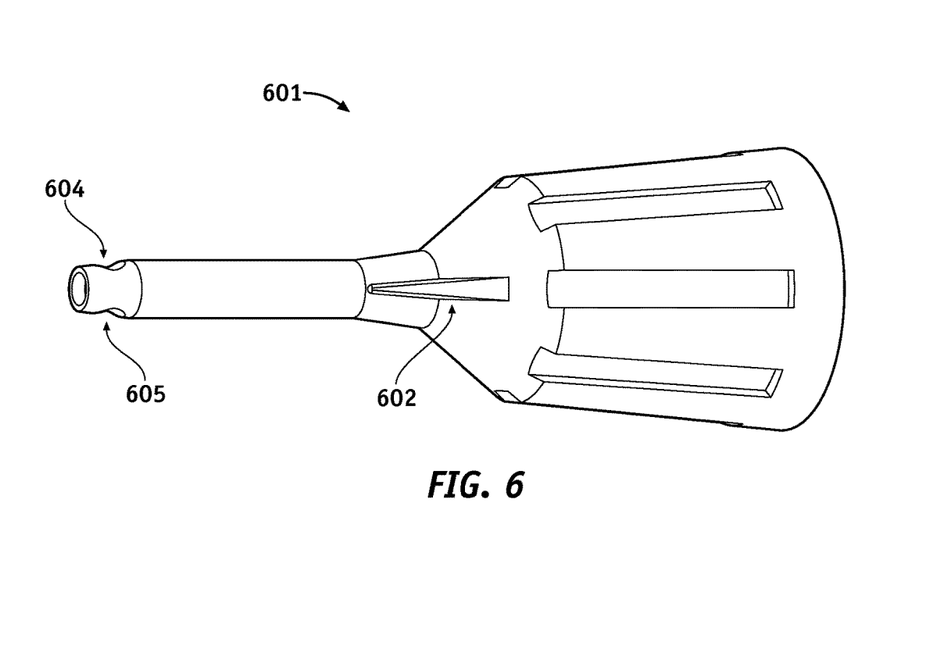
FIG. 6 illustrates markings in the form of two raised ribs substantially aligned with the fluid openings or ports.
Figure 7:
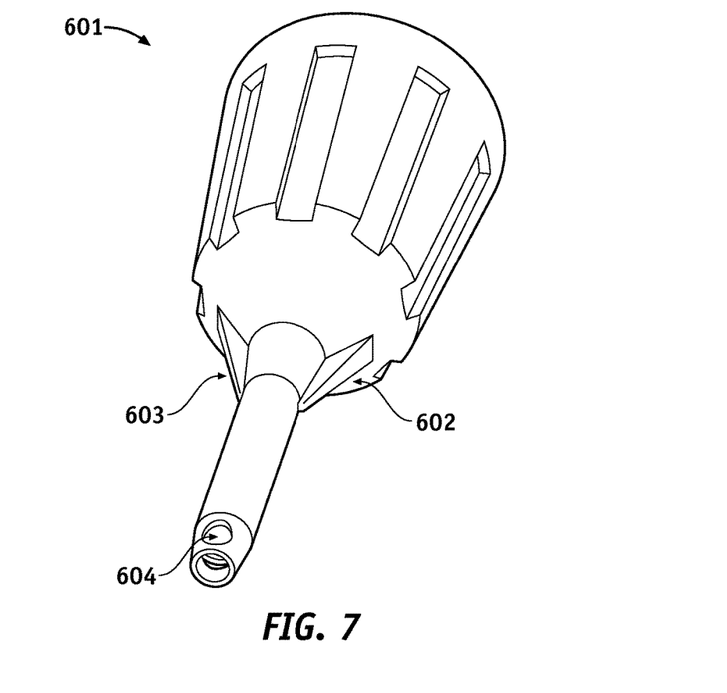
FIG. 7 illustrates markings in the form of two raised ribs oriented at approximately 90 degrees relative to the fluid openings or ports.

FIGS. 6 and 7 show markings embodied as two raised outer ribs such as rib 602 (the other rib, approximately 180 degrees away from rib 602, is not shown in FIG. 6) on sleeve 601, where each rib such as rib 602 is approximately radially oriented 90 degrees from port openings 604 and 605. An imaginary extended line along the long axis of each raised outer rib such as rib 602 thus passes halfway between the port locations. This 90 degree orientation between the visual reference marker or raised outer rib 602 and port openings 604 and 605 allows the user or surgeon to know the rotational orientation of port openings 604 and 605 when they are at their least visible. For example, when the raised outer ribs such as rib 602 are rotated to be right and left facing when viewed in a microscope, port openings 604 and 605 are only partially visible. This 90 degree offset between ribs and port openings cause the ports to be directed perpendicular to the surgeon's field of view through the surgical microscope when the marking, such as rib 602, is viewable so that the fluid flow runs circumferentially around the eye's anterior chamber at a set depth relative to the corneal incision. Again, color of the ribs may be similar to or different from the color of the sleeve and may be provided in a different form, including but not limited to a groove, set of raised items, or as otherwise disclosed herein.

Figure 8:
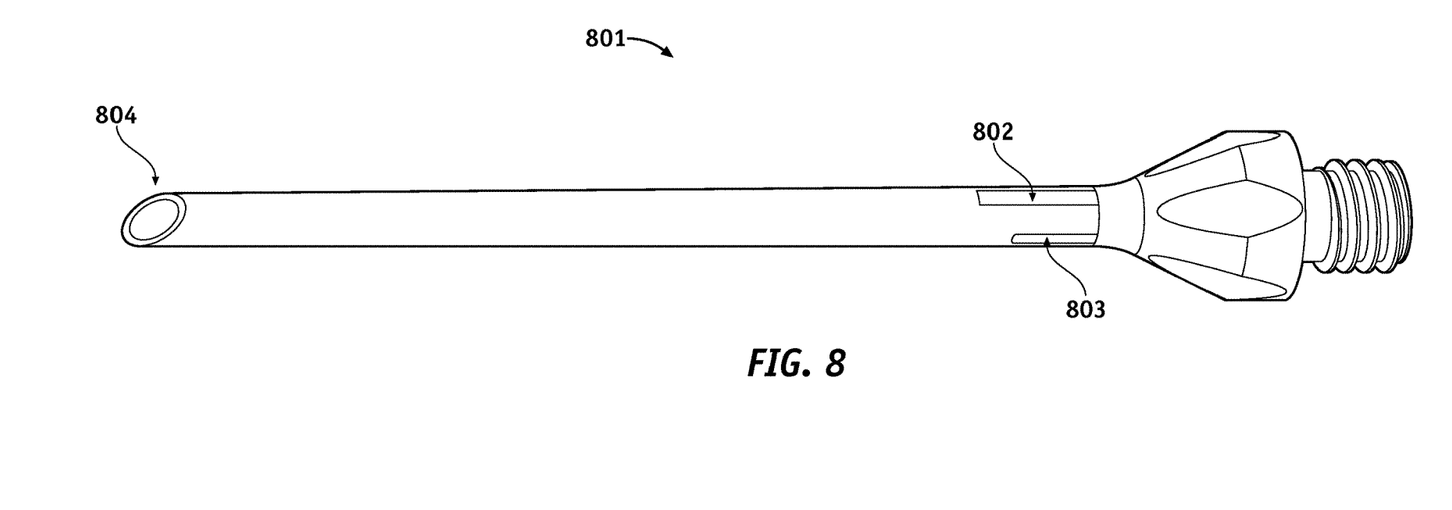
FIG. 8 shows a beveled phacoemulsification needle having markings represented by colored stripes.

FIG. 8 illustrates an embodiment of a needle wherein a sleeve is not employed, such as in the case where a separate irrigation device or handpiece is provided. FIG. 8 shows a beveled phacoemulsification needle 801 having markings represented by "stripes" 802 and 803, where stripes 802 and 803 may be of a contrasting color to the locally surrounding surface color of the phacoemulsification needle 801. For example, stripe 802 may be black and stripe 803 may be white, while the general exterior color of phaco needle 801 is a neutral color such as white or grey. The "stripes" or any markings discussed herein may also take the form of grooves, dots, raised portions, and/or may be of varying textures which are visible to the surgeon. One orientation of stripes 802 and 803 is relative to beveled tip 804 of phaco needle 801. Stripes 802 and 803 may be provided such that an imaginary extended line along the long axis of the stripes 802 and 803 corresponds to a desired bevel rotational orientation.

As noted, multiple different stripes of varying color, width, and/or length are presented in FIG. 8 and provide a visual indication to the surgeon of the direction the tip or bevel 804 is facing. For example, if the long dark stripe 802 is viewable to the surgeon under a microscope, she knows that the orientation is correct, but if a shorter, lighter colored stripe 803 is viewable, she knows she should rotate the device 90 degrees counterclockwise in this example to locate the long black stripe and thus properly orient the phaco needle 801.

The angle of the bevel of beveled tip 804 of phaco needle 801 produces a circular or oval opening that faces in one direction, and in some applications the circular or oval opening is oriented upward or toward the surgeon when viewed through a microscope. A sample orientation of a beveled tip 904 when viewed through a microscope is presented in FIG. 9, where needle 901 includes stripes 902 and 903 and the opening of the beveled tip 904 is pointed upward or toward the surgeon. Again, stripe 902 and stripe 903 represent markers or visual markings that enable the surgeon to verify a proper, acceptable, and/or desired orientation of a tip, such as beveled tip 904, when the distal portion of the device is not viewable or difficult to ascertain during an ocular surgical procedure. Other orientations and markings may be employed depending on various factors, such as the desired fluid flow direction.

Figure 9:
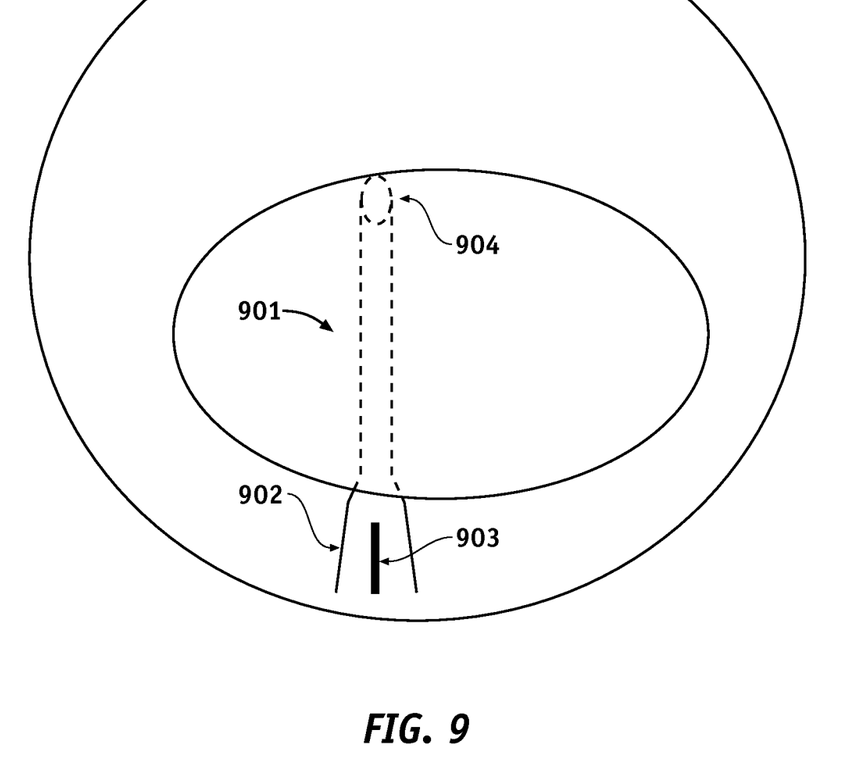
FIG. 9 illustrates orientation of a beveled phacoemulsification needle and an associated marking when employed in an ocular surgical procedure as the device would be expected to be viewed by a surgeon through a microscope.

The depiction of FIG. 8 shows that the visual reference markers can convey specific orientation of bevel tip 904 when such markers, here represented by stripes 902 and 903, are provided using any one or a combination of multiple visually distinctive aspects, including but not limited to color (e.g., blue vs. black, such as stripe 902 being blue and stripe 903 being black, with needle 901 a light color such as off-white or grey), relative length (e.g., long vs. short), relative width (e.g., wide vs. narrow), and feature shape (e.g., pointed vs. rounded or blunt). Varying markers or visual markings can therefore be provided, thus producing a measure of the quality of the orientation of the device and potentially may provide instructions as to how the user should rotate or reorient the device to obtain improved fluid directional flow.

Figure 10:
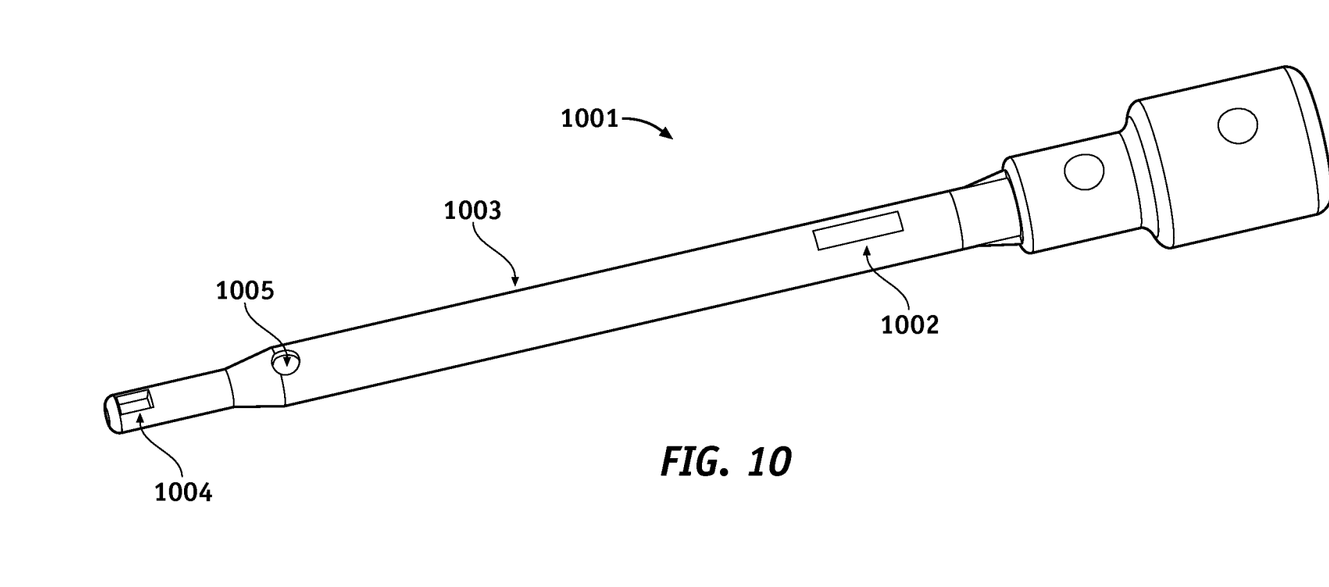
FIG. 10 illustrates a vitrectomy handpiece irrigation sleeve having a marking in the form of stripe coaxially placed on a vitrectomy cutter shaft in line with a distal radially-directed aspiration/cutting port.

FIG. 10 illustrates a vitrectomy cutter 1001 having a marking in the form of stripe 1002 coaxially placed on shaft 1003 with a distal radially-directed aspiration/cutting port 1004. Stripe 1002 may be of contrasting color and can be intentionally and consistently placed directly or perpendicularly rotationally aligned such that an imaginary extended line along the long axis of the "stripes" passes through the distal radially-directed aspiration/cutting port 1004 and/or irrigation port 1005. Irrigation port 1005 may be located at any position on and/or around vitrectomy cutter 1001, including towards or near aspiration/cutting port 1004 or offset from aspiration/cutting port 1005. The marking may also be placed in along the longitudinal axis of (or in line with) aspiration/cutting port 1004 and/or irrigation port 1005. Again, multiple markings, such as stripes, raised ribs, dots, circles, or other visual indicators may be provided, including markings that indicate the quality of the orientation of the device (unacceptable, good, better, best) and provide instructions or indications for rotation and/or proper orientation. Different marking characteristics (color, length, relative width, shape) may be provided at different positions around the periphery of the device.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A device configured for use in an ocular surgical procedure, comprising:
    a proximal portion substantially oriented along a central axis;
    a needle that includes a distal portion substantially oriented along the central axis and comprising a first fluid opening that is formed at a predetermined orientation with regard to the central axis;
    a sleeve that includes a second fluid opening and a third fluid opening, wherein the second fluid opening and the third fluid opening are orthogonal to the first fluid opening;
    at least one first visual marking located on a surface of the proximal portion suitable for providing a first visual indication of the predetermined orientation when the first fluid opening is at least partially obscured during the ocular surgical procedure;
    at least one second visual marking located on a surface of the sleeve and suitable for providing a second visual indication of a location of the second fluid opening; and
    at least one third visual marking located on the same surface of the sleeve as the at least one second visual marking and suitable for providing a third visual indication of a location of the third fluid opening.

2. The device of claim 1, wherein the second fluid opening and the third fluid opening are oriented approximately 180 degrees apart, and wherein at least one visual marking extends in a direction orthogonal to the central axis.

3. The device of claim 1, wherein the at least one first visual marking comprises a plurality of visual markings, wherein at least one first visual marking differs in quality from the at least one second visual marking and the at least one third visual marking, thereby providing an indication of quality of orientation of the device.

4. The device of claim 1, wherein at least one first visual marking comprises a colored marking differing in color from a color of the distal portion.

5. The device of claim 1, wherein the needle is a phacoemulsification needle.

6. A sleeve device configured for use with a needle in a surgical procedure, the needle forming a central axis, the sleeve device comprising:
    a proximal sleeve portion substantially oriented about the central axis;
    a distal sleeve portion substantially oriented about the central axis and comprising:
        an opening configured to enable the needle to pass therethrough, wherein the needle includes a first opening formed at a predetermined orientation with respect to the central axis
        a second opening orthogonal to the first opening that is configured to enable fluid to pass therethrough, and
        a third opening orthogonal to the first opening that is configured to enable fluid to pass therethrough;
    at least one first visual marking located on a surface of the proximal sleeve portion suitable for providing a visual indication of the predetermined orientation when the first opening is at least partially obscured during the surgical procedure;
    at least one second visual marking located on a surface of the sleeve for providing a second visual indication of a location of the second opening; and
    at least one third visual marking located on the same surface of the sleeve as the at least one second visual marking for providing a third visual indication of a location of the third opening.

7. The device of claim 6, wherein the second opening and the third opening are oriented approximately 180 degrees apart, and wherein at least one visual marking extends in a direction orthogonal to the central axis.

8. The device of claim 6, wherein the at least one first visual marking comprises a plurality of visual markings, wherein at least one first visual marking differs in quality from the at least one second visual marking and the at least one third visual marking, thereby providing an indication of quality of orientation of the sleeve device and the needle.

9. The device of claim 6, wherein the needle is a phacoemulsification needle.

10. The device of claim 6, wherein at least one first visual marking comprises a colored marking differing in color from a color of the proximal portion.

11. A device configured for use in a surgical procedure, comprising:
    a proximal portion oriented along a central axis;
    a needle that includes a distal portion oriented along the central axis and comprising a first opening formed in a predetermined orientation relative to a plane that crosses the central axis, wherein the first opening is configured to permit fluid to pass therethrough;
    a sleeve that includes a second opening formed orthogonal to the first opening, wherein the second opening is configured to permit fluid to pass therethrough, and a third opening formed orthogonal to the first opening, wherein the third opening is configured to permit fluid to pass therethrough;

at least one first visual marking comprising at least one protrusion formed in and raised outward from a surface of the proximal portion and located at the proximal portion and suitable for providing a visual indication of the predetermined orientation when the first opening is at least partially obscured during the surgical procedure;

at least one second visual marking located on a surface of the sleeve and suitable for providing a second visual indication of a location of the second opening; and at least one third visual marking located on the same surface of the sleeve as the at least one second visual marking and suitable for providing a third visual indication of a location of the third opening.

12. The device of claim 11, wherein the second opening and the third opening are oriented approximately 180 degrees apart and are orthogonal to the first opening, and wherein at least one first visual marking extends in a direction orthogonal to the central axis.

13. The device of claim 11, wherein the at least one first visual marking comprises a plurality of visual markings, wherein at least one first visual marking differs in quality from the at least one second visual marking and the at least one third visual marking, thereby providing an indication of quality of orientation of the device.

14. The device of claim 11, wherein the needle is a phacoemulsification needle.

15. The device of claim 11, wherein at least one first visual marking comprises a colored marking differing in color from a color of the proximal portion.

16. The device of claim 1, wherein the at least one first visual marking comprises at least one protrusion formed in and raised outward from the proximal portion, wherein the at least one protrusion has a first proximal end and proceeds axially along the central axis to a second distal end.

17. The device of claim 6, wherein the at least one first visual marking comprises at least one protrusion formed in and raised outward from the proximal portion, wherein the at least one protrusion has a first proximal end and proceeds axially along the central axis to a second distal end.

18. The device of claim 1, wherein the predetermined orientation is a beveled angle.

19. The device of claim 6, wherein the predetermined orientation is a beveled angle.

20. The device of claim 11, wherein the predetermined orientation is a beveled angle.

* * * * *